(12) United States Patent
Minty

(10) Patent No.: US 12,127,813 B2
(45) Date of Patent: Oct. 29, 2024

(54) DETECTION OF DISEASES VIRUSES AND OTHER BIOLOGICAL INFECTIONS

(71) Applicant: Colin Minty, Didsbury (CA)

(72) Inventor: Colin Minty, Didsbury (CA)

(73) Assignee: Colin Minty, Didsbury (CA)

( * ) Notice: Subject to any disclaimer, the term of this patent is extended or adjusted under 35 U.S.C. 154(b) by 766 days.

(21) Appl. No.: 17/223,451

(22) Filed: Apr. 6, 2021

(65) Prior Publication Data

US 2021/0345881 A1 Nov. 11, 2021

Related U.S. Application Data

(60) Provisional application No. 63/006,659, filed on Apr. 7, 2020.

(51) Int. Cl.
*A61B 5/00* (2006.01)
(52) U.S. Cl.
CPC .......... *A61B 5/0075* (2013.01); *A61B 5/0077* (2013.01); *A61B 5/41* (2013.01); *A61B 5/7246* (2013.01); *A61B 5/742* (2013.01)

(58) Field of Classification Search
CPC ....... A61B 5/0075; A61B 5/0077; A61B 5/41; A61B 5/7246; A61B 5/742
See application file for complete search history.

(56) References Cited

U.S. PATENT DOCUMENTS

| | | | |
|---|---|---|---|
| 2006/0030031 A1* | 2/2006 | Modrovich | A61B 5/1486 435/287.2 |
| 2018/0057852 A1* | 3/2018 | Takats | A61B 5/0075 |
| 2023/0143849 A1* | 5/2023 | Takáts | A61B 5/0075 250/282 |

* cited by examiner

*Primary Examiner* — John J Lee

(57) ABSTRACT

The purpose of the invention is to provide rapid non contact detection of diseases, viruses, and other biological infections.

A method of detecting diseases, viruses, and other biological infections is disclosed. The method comprises a gas analyzer detecting the chemical release emitted from a living body. The gas analyzer is an optical sensor and is located near the target. The gas analyzer then processes the readings using internal software to give an instant value of the concentration of the target gas. The gas analyzer would then output a signal indicating the presence of the gas. The gas analyzer can also incorporate a video camera for aiming purposes and recording images.

2 Claims, 1 Drawing Sheet

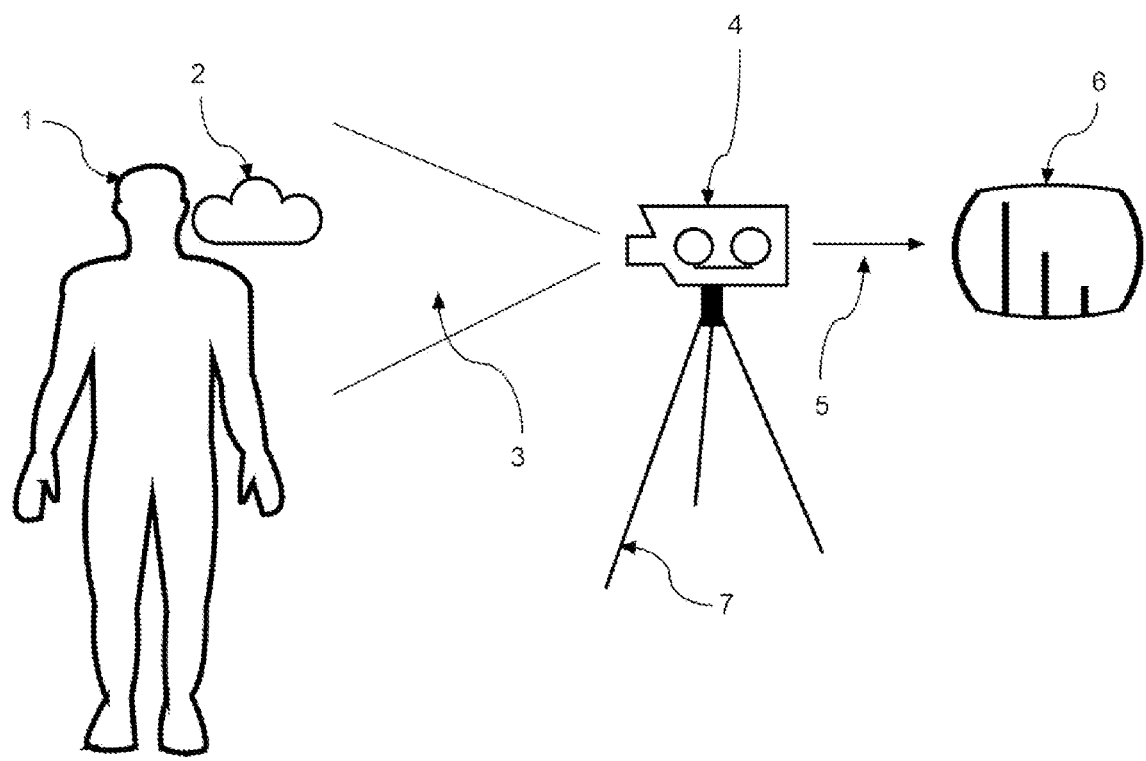

DETECTION OF DISEASES VIRUSES AND OTHER BIOLOGICAL INFECTIONS

CROSS-REFERENCE TO RELATED APPLICATIONS

Not Applicable

BACKGROUND OF THE INVENTION

This invention relates to the detection of chemicals released from a living body. More particularly this invention relates to the detection of diseases, viruses, and other biological infections.

The difficulty of detecting diseases, viruses, or other biological infections has been a problem existent throughout medical history. Methods involving the physical sampling and analyzing of materials are time-consuming and involve close contact with the patient. This invention provides non-contact sampling and instant results.

With this method, the detection of diseases, viruses, and other biological infections is noncontact and rapid. Currently, detection of diseases, viruses, and other biological infections requires with close contact a sample from the patient, preparation of the sample and analysis In an infrared system, heat dissipated by the living body is employed at airports and other crowded locations. The problem with an infrared system is that it yields poor results if fever is slight, or medication is used. Another limitation is the image is not clear for identification use. Recent pandemic conditions generate demand for a more effective means of detecting these types of illnesses.

It is an object of this invention to disclose a more effective means of detecting diseases, viruses, and other biological infections. It is an object of this invention to disclose a system that can more quickly and inexpensively, identify potential positive results. It is a further object of this invention to disclose a data storage and retrieval method and apparatus which allows fast access and physical identification of infection.

This invention can be rapidly deployed by medical personnel and other government organizations

BRIEF SUMMARY OF THE INVENTION

The purpose of the invention is to provide rapid non-contact detection of diseases, viruses, and other biological infections. A method of detecting diseases, viruses, and other biological infections is disclosed. The method comprises a gas analyzer detecting the chemical release emitted from a living body. The gas analyzer is an optical sensor and is located near the target. The gas analyzer then processes the readings using internal software to give an instant value of the concentration of the target gas. The gas analyzer would then output a signal indicating the presence of the gas. The gas analyzer can also incorporate a video camera for aiming purposes and recording images.

BRIEF DESCRIPTION OF THE SEVERAL VIEWS OF THE DRAWING

FIG. 1 is a perspective view of the typical deployment of the gas analyzer.

This FIGURE shows the gas analyzer that would be used and mounted on a tripod. This would be aimed at the patient giving an analysis of the result interpretations.

1 A living being to be analyzed.
2 Chemical released from the subject.
3 Field of view for the gas analyzer.
4 The gas analyzer.
5 Data output to display.
6 The displayed results.
7 The tripod or mounting device for the gas analyzer

DETAILED DESCRIPTION

One aspect of this invention provides for a method of detection comprising of the following steps: surveillance of individuals in appropriate locations; continuously collecting measurements which test for high concentrations of the chemical being measured; processing the results for display and storage; concurrently recording the video image to correlate the data. In one aspect of this invention, the computer is programmed to graphically display the correlated data on its display.

An apparatus to perform the above-described method is provided. A preferred aspect of this apparatus provides for an air analyzer which is set up to differentiate between chemical concentrations in the air sample and the ambient air.

Various other objects, advantages, and features of this invention will become apparent to those skilled in the art from the following description in conjunction with accompanying drawings.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

Turning now to the drawings and more particularly to FIG. 1, we have a typical setup of the disease, virus, and other biological infection monitoring system, hereinafter called the DVMS.

The DVMS is housed in a semi-portable enclosure which can be mounted on a 7 tripod or mounted to a fixed structure. As 1 humans or other animals walk 3 through the field of view, the field of view being approximately 30 degrees, the analyzer will detect the 2 anomaly if a chemical is emitting from the test subject. An integral simultaneous video recording is also used.

The DVMS 4 preferred gas analyzer for detection uses a Fourier Transform Infrared (FTIR) spectrometer, but other gas analyzers using different technologies may be used; however, the GASCAM manufactured by Airwave Electronics Ltd. in Didsbury, Canada is preferred for its sensitivity, instant response time, high reliability, and low maintenance. This analyzer 5 has improved temperature stability and radio frequency interference reduction. The gas analyzer has an integral computer that matches the emission spectrum of that of the target chemical compound, additionally, the magnitude of the signal is displayed on the GASCAM integral display or a 6 remote computer, the video image is also displayed on the GASCAM integral display or a 6 remote computer While the invention has been described with specific embodiments thereof, it will be understood that this description is intended to illustrate, and not to limit the scope of the invention which is defined by the following claims.

The embodiments of the invention in which an exclusive property or privilege is claimed are defined as follows:

1. A method for detecting diseases, viruses, and biological infections, comprising:
   mounting a device, wherein the device includes a gas analyzer, an integral computer, and a video camera, onto a tripod or to a fixed structure;
      wherein, the gas analyzer includes a Fourier Transform Infrared (FTIR) spectrometer;
   identifying, a test subject, wherein the test subject is a human or a non-human animal, within a field of view of the gas analyzer;
   detecting, by the gas analyzer, a signal from the test subject, wherein the signal includes one or more emission spectrums;
   matching, by the integral computer, the one or more emission spectrums to one or more target chemical compounds;
   in response to the event that at least one of the one or more emission spectrums matches at least one of the one or more target chemical compounds, noting an anomaly;
   taking, by the video camera, a video of the test subject;
   displaying, on a screen of the integral computer, the signal and the video;
   displaying, on the remote computer, the signal and the video.

2. A system for detecting diseases, viruses, and biological infections, comprising:
   a gas analyzer,
      wherein, the gas analyzer includes a Fourier Transform Infrared (FTIR) spectrometer;
      wherein, the gas analyzer is configured to detect a signal from a test subject within a field of view of the gas analyzer, wherein the test subject is a human or a non-human animal;
      wherein, the signal contains one or more emission spectrums;
   a video camera,
      wherein, the video camera is configured to:
         take a video of the test subject;
   an integral computer;
      wherein, the integral computer is configured to:
         match the one or more emission spectrums to one or more target chemical compounds;
         in response to the event that at least one of the one or more emission spectrums matches at least one of the one or more target chemical compounds, note an anomaly;
         display the signal and the video on a screen of the integral computer;
   a remote computer,
      wherein, the remote computer is configured to:
         display the signal and the video;
   a semi-portable enclosure housing the gas analyzer, the video camera, and the integral computer.

* * * * *